United States Patent [19]
Porter et al.

[11] Patent Number: 4,692,234
[45] Date of Patent: Sep. 8, 1987

[54] ANTIFOULANTS FOR THERMAL CRACKING PROCESSES

[75] Inventors: Randall A. Porter; Larry E. Reed, both of Bartlesville, Okla.

[73] Assignee: Phillips Petroleum Company, Bartlesville, Okla.

[21] Appl. No.: 849,644

[22] Filed: Apr. 9, 1986

[51] Int. Cl.$^4$ .................... C10G 9/16; C23C 18/12
[52] U.S. Cl. ...................... 208/48 AA; 106/1.12; 106/1.25; 208/52 CT; 502/170; 502/171; 502/242; 502/246
[58] Field of Search .................. 106/15.05, 1.12, 1.25; 208/48 AA, 52 CT; 502/153, 154, 167, 168, 162, 170, 171, 174, 200, 216, 224, 227, 242, 246

[56] References Cited

U.S. PATENT DOCUMENTS

| 1,547,236 | 7/1925 | Reyerson | 502/246 |
| 1,847,095 | 3/1932 | Mittasch et al. | |
| 2,063,596 | 12/1936 | Feiler | 196/133 |
| 2,336,054 | 12/1943 | Atkinson | 260/683 |
| 2,354,163 | 7/1944 | Weizmann et al. | 196/47 |
| 3,531,394 | 9/1970 | Koezman | 208/48 |
| 4,404,087 | 9/1983 | Reed et al. | 208/48 AA |
| 4,410,418 | 10/1983 | Kukes et al. | 208/48 R |
| 4,466,884 | 8/1984 | Occelli et al. | 208/52 CT |
| 4,507,196 | 3/1985 | Reed et al. | 208/48 AA |
| 4,511,405 | 4/1985 | Reed et al. | 106/15.05 |
| 4,545,893 | 10/1985 | Porter et al. | 208/48 R |
| 4,551,227 | 11/1985 | Porter et al. | 208/48 AA |
| 4,552,643 | 11/1985 | Porter et al. | 208/48 AA |

OTHER PUBLICATIONS

Chemical Abstracts, vol. 95, Abstract No. 28896g (Parikh et al.).

Primary Examiner—Robert A. Wax
Attorney, Agent, or Firm—J. Michael Simpson

[57] ABSTRACT

The formation of carbon on metals exposed to hydrocarbons in a thermal cracking process is reduced by contacting such metals with an antifoulant selected from the group consisting of a combination of tin and silicon, a combination of antimony and silicon and a combination of tin, antimony and silicon.

30 Claims, 3 Drawing Figures

ANTIFOULANTS FOR THERMAL CRACKING PROCESSES

This invention relates to processes for the thermal cracking of a gaseous stream containing hydrocarbons. In one aspect this invention relates to a method for reducing the formation of carbon on the cracking tubes in furnaces used for the thermal cracking of a gaseous stream containing hydrocarbons and in any heat exchangers used to cool the effluent flowing from the furnaces. In another aspect this invention relates to particular antifoulants which are useful for reducing the rate of formation of carbon on the walls of such cracking tubes and in such heat exchangers.

The cracking furnace forms the heart of many chemical manufacturing processes. Often, the performance of the cracking furnace will carry the burden of the major profit potential of the entire manufacturing process. Thus, it is extremely desirable to maximize the performance of the cracking furnace.

In a manufacturing process such as the manufacture of ethylene, a feed gas such as ethane and/or propane and/or naphtha is fed into the cracking furnace. A diluent fluid such as steam is usually combined with the feed material being provided to the cracking furnace. Within the furnace, the feed stream which has been combined with the diluent fluid is converted to a gaseous mixture which primarily contains hydrogen, methane, ethylene, propylene, butadiene, and small amounts of heavier gases. At the furnace exit this mixture is cooled, which allows removal of most of the heavier gases, and compressed.

The compressed mixture is routed through various distillation columns where the individual components such as ethylene are purified and separated. The separated products, of which ethylene is the major product, then leave the ethylene plant to be used in numerous other processes for the manufacture of a wide variety of secondary products.

The primary function of the cracking furnace is to convert the feed stream to ethylene and/or propylene. A semi-pure carbon which is termed "coke" is formed in the cracking furnace as a result of the furnace cracking operation. Coke is also formed in the heat exchangers used to cool the gaseous mixture flowing from the cracking furnace. Coke formation generally results from a combination of a homogeneous thermal reaction in the gas phase (thermal coking) and a heterogeneous catalytic reaction between the hydrocarbon in the gas phase and the metals in the walls of the cracking tubes or heat exchangers (catalytic coking).

Coke is generally referred to as forming on the metal surfaces of the cracking tubes which are contacted with the feed stream and on the metal surfaces of the heat exchangers which are contacted with the gaseous effluent from the cracking furnace. However, it should be recognized that coke may form on connecting conduits and other metal surfaces which are exposed to hydrocarbons at high temperatures. Thus, the term "Metals" will be used hereinafter to refer to all metal surfaces in a cracking process which are exposed to hydrocarbons and which are subject to coke deposition.

A normal operating procedure for a cracking furnace is to periodically shut down the furnace in order to burn out the deposits of coke. This downtime results in a substantial loss of production. In addition, coke is an excellent thermal insulator. Thus, as coke is deposited, higher furnace temperatures are required to maintain the gas temperature in the cracking zone at a desired level. Such higher temperatures increase fuel consumption and will eventually result in shorter tube life.

Another problem associated with carbon formation is erosion of the Metals, which occurs in two fashions. First, it is well known that in the formation of catalytic coke the metal catalyst particle is removed or displaced from the surface and entrained within the coke. This phenomenon results in extremely rapid metal loss and, ultimately, Metals failure. A second type of erosion is caused by carbon particles that are dislodged from the tube walls and enter the gas stream. The abrasive action of these particles can be particularly severe on the return bends in the furnace tube.

Yet another and more subtle effect of coke formation occurs when coke enters the furnace tube alloy in the form of a solid solution. The carbon then reacts with the chromium in the alloy and chromium carbide precipitates. This phenomenon, known as carburization, causes the alloy to lose its original oxidation resistance, thereby becoming susceptible to chemical attack. The mechanical properties of the tube are also adversely affected. Carburization may also occur with respect to iron and nickel in the alloys.

It is thus an object of this invention to provide a method for reducing the formation of coke on the Metals. It is another object of this invention to provide particular antifoulants which are useful for reducing the formation of carbon on the Metals.

In accordance with the present invention, an antifoulant selected from the group consisting of a combination of tin and silicon, a combination of antimony and silicon and a combination of tin, antimony and silicon is contacted with the Metals either by pretreating the Metals with the antifoulant, adding the antifoulant to the hydrocarbon feedstock flowing to the cracking furnace or both. The use of the antifoulant substantially reduces the formation of coke on the Metals which substantially reduces the adverse consequences which attend such coke formation.

Other objects and advantages of the invention will be apparent from the foregoing brief description of the invention and the claims as well as the detailed description of the drawings in which:

Figure 1:
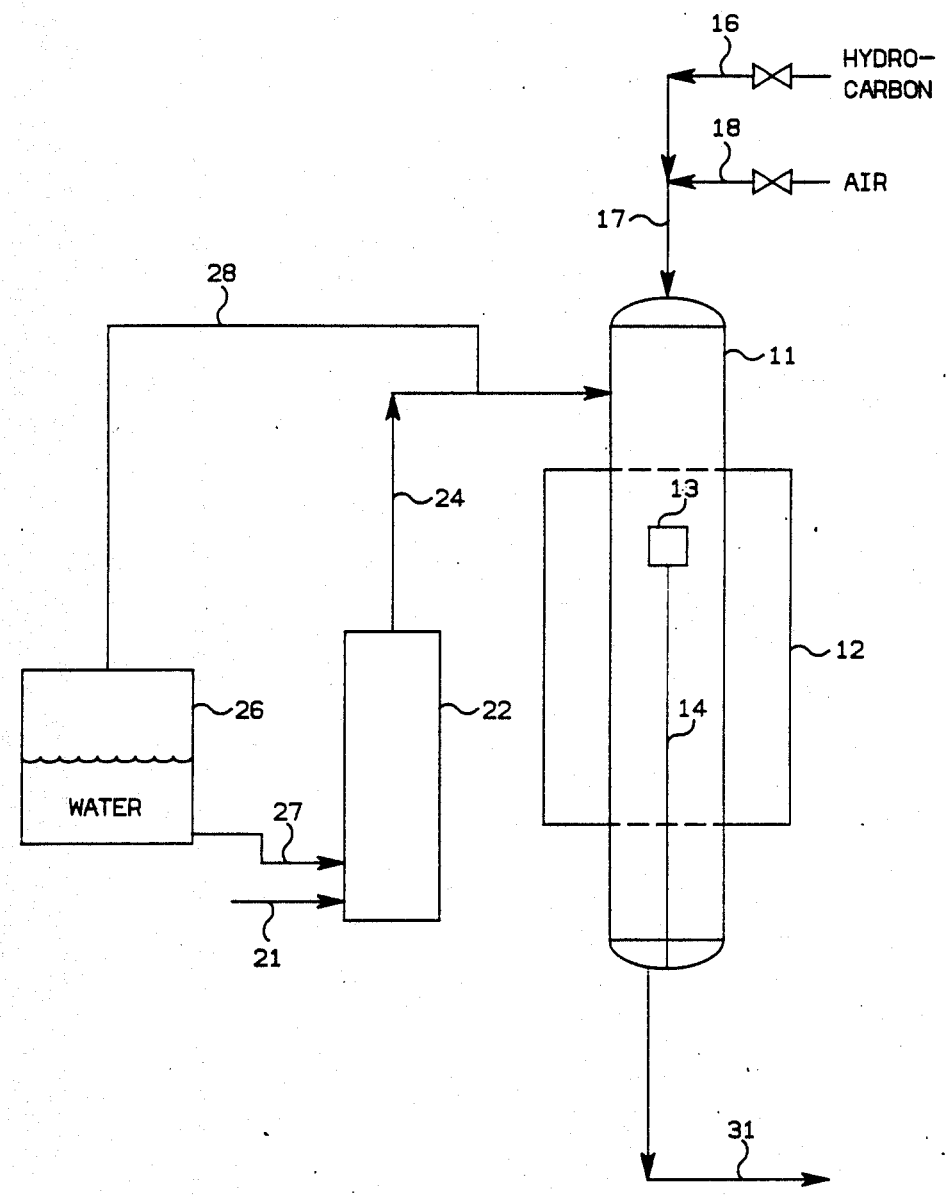
FIG. 1 is a diagrammatic illustration of the test apparatus used to test the antifoulants of the present invention.

The invention is described in terms of a cracking furnace used in a process for the manufacture of ethylene. However, the applicability of the invention described herein extends to other processes wherein a cracking furnace is utilized to crack a feed material into some desired components and the formation of coke on the walls of the cracking tubes in the cracking furnace or other metal surfaces associated with the cracking process is a problem.

Any suitable form of silicon may be utilized in the combination of antimony and silicon antifoulant, the combination of tin and silicon antifoulant or the combination of tin, antimony and silicon antifoulant. Elemental silicon, inorganic silicon compounds and organic silicon compounds as well as mixtures of any two or more thereof are suitable sources of silicon. The term "silicon" generally refers to any one of these silicon sources.

Examples of some inorganic silicon compounds that can be used include the halides, nitrides, hydrides, oxides and sulfides of silicon, silicic acids and alkali metal salts thereof. Of the inorganic silicon compounds, those which do not contain halogen are preferred.

Examples of organic silicon compounds that may be used include compounds of the formula

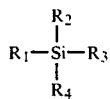

wherein $R_1$, $R_2$, $R_3$, and $R_4$ are selected independently from the group consisting of hydrogen, halogen, hydrocarbyl, and oxyhydrocarbyl and wherein the compound's bonding may be either ionic or covalent. The hydrocarbyl and oxyhydrocarbyl radicals can have from 1-20 carbon atoms which may be substituted with halogen, nitrogen, phosphorus, or sulfur. Exemplary hydrocarbyl radicals are alkyl, alkenyl, cycloalkyl, aryl, and combinations thereof, such as alkylaryl or alkylcycloalkyl. Exemplary oxyhydrocarbyl radicals are alkoxide, phenoxide, carboxylate, ketocarboxylate and diketone (dione). Suitable organic silicon compounds include trimethylsilane, tetramethylsilane, tetraethylsilane, triethylchlorosilane, phenyltrimethylsilane, tetraphenylsilane, ethyltrimethoxysilane, propyltriethoxysilane, dodecyltrihexoxysilane, vinyltriethyoxysilane, tetramethoxyorthosilicate, tetraethoxyorthosilicate, polydimethylsiloxane, polydiethylsiloxane, polydihexylsiloxane, polycyclohexylsiloxane, polydiphenylsiloxane, polyphenylmethylsiloxane, 3-chloropropyltrimethoxysilane, and 3-aminopropyltriethoxysilane. At present tetraethylorthosilicate is preferred.

Organic silicon compounds are particularly preferred because such compounds are soluble in the feed material and in the diluents which are preferred for preparing pretreatment solutions as will be more fully described hereinafter. Also, organic silicon compounds appear to have less of a tendency towards adverse effects on the cracking process than do inorganic silicon compounds.

Any suitable form of antimony may be utilized in the combination of antimony and silicon antifoulant or in the combination of tin, antimony and silicon antifoulant. Elemental antimony, inorganic antimony compounds and organic antimony compounds as well as mixtures of any two or more thereof are suitable sorces of antimony. The term "antimony" generally refers to any one of these antimony sources.

Examples of some inorganic antimony compounds which can be used include antimony oxides such as antimony trioxide, antimony tetroxide, and antimony pentoxide; antimony sulfides such as antimony trisulfide and antimony pentasulfide; antimony sulfates such as antimony trisulfate; antimonic acids such as metaantimonic acid, orthoantimonic acid and pyroantimonic acid; antimony halides such as antimony trifluoride, antimony trichloride, antimony tribromide, antimony triiodide, antimony pentafluoride and antimony pentachloride; antimonyl halides such as antimonyl chloride and antimonyl trichloride. Of the inorganic antimony compounds, those which do not contain halogen are preferred.

Examples of some organic antimony compounds which can be used include antimony carboxylates such as antimony triformate, antimony trioctoate, antimony triacetate, antimony tridodecanoate, antimony trioctadecanoate, antimony tribenzoate, and antimony tris(-cyclohexenecarboxylate); antimony thiocarboxylates such as antimony tris(thioacetate), antimony tris(dithioacetate) and antimony tris(dithiopentanoate); antimony thiocarbonates such as antimony tris(O-propyl dithiocarbonate); antimony carbonates such as antimony tris(ethyl carbonates); trihydrocarbylantimony compounds such as triphenylantimony; trihydrocarbylantimony oxides such as triphenylantimony oxide; antimony salts of phenolic compounds such as antimony triphenoxide; antimony salts of thiophenolic compounds such as antimony tris(-thiophenoxide); antimony sulfonates such as antimony tris(benzenesulfonate) and antimony tris(p-toluenesulfonate); antimony carbamates such as antimony tris(diethylcarbamate); antimony thiocarbamates such as antimony tris(dipropyldithiocarbamate), antimony tris(-phenyldithiocarbamate) and anitmony tris(butylthiocarbamate); antimony phosphites such as antimony tris(-diphenyl phosphite); antimony phosphates such as antimony tris(-dipropyl) phosphate; antimony thiophosphates such as antimony tris(O,O-dipropyl thiophosphate) and antimony tris(O,O-dipropyl dithiophosphate) and the like. At present antimony 2-ethylhexanoate is preferred. Again, as with silicon, organic compounds of anitmony are preferred over inorganic compounds.

Any suitable form of tin my be utilized in the combination of tin and silicon antifoulant or in the combination of tin, antimony and silicon antifoulant. Elemental tin, inorganic tin compounds and organic tin compounds as well as mixtures of any two or more thereof are suitable sources of tin. The term "tin" generally refers to any one of these tin sources.

Examples of some inorganic tin compounds which can be used include tin oxides such as stannous oxide and stannic oxide; tin sulfides such as stannous sulfide and stannic sulfide; tin sulfates such as stannous sulfate and stannic sulfate; stannic acids such as metastannic acid and thiostannic acid; tin halides such as stannous fluoride, stannous chloride, stannous bromide, stannous iodide, stannic fluoride, stannic chloride, stannic bromide and stannic iodide; tin phosphates such as stannic phosphate; tin oxyhalides such as stannous oxychloride and stannic oxychloride; and the like. Of the inorganic tin compounds those which do not contain halogen are preferred as the source of tin.

Examples of some organic tin compounds which can be used include tin carboxylates such as stannous formate, stannous acetate, stannous butyrate, stannous octoate, stannous decanoate, stannous oxalate, stannous benzoate, and stannous cyclohexanecarboxylate; tin thiocarboxylates such as stannous thioacetate and stannous dithioacetate; dihydrocarbyltin bis(hydrocarbyl mercaptoalkanoates) such as dibutyltin -bis(isooctyl mercaptoacetate) and dipropyltin bis(butyl mercaptoacetate); tin thiocarbonates such as stannous O-ethyl dithiocarbonate; tin carbonates such as stannous propyl carbonate; tetrahydrocarbyltin compounds such as tetrabutyltin, tetraoctyltin, tetradodecyltin, and tetraphenyltin; dihydrocarbyltin oxides such as dipropyltin oxide; dibutyltin oxide, dioctyltin oxide, and diphenyltin oxide; dihydrocarbyltin bis(hydrocarbyl mercaptide)s such as dibutyltin bis(dodecyl mercaptide); tin salts of phenolic compounds such as stannous thiophenoxide; tin sulfonates such as stannous benzenesulfonate and stannous-p- toluenesulfonate; tin carbamates such as stannous diethylcarbamate; tin thiocarbamates such as stannous propylthiocarbamate and stannous diethyldithiocarbamate; tin phosphites such as stannous diphenyl phosphite; tin phosphates such as stannous dipropyl phosphate; tin thiophosphates such as stannous O,O-dipropyl thiophosphate, stannous O,O-dipropyl dithiophosphate and stannic O,O-dipropyl dithiophosphate, dihydrocarbyltin bis(O,O-dihydrocarbyl thiophosphate)s such as dibutyltin bis(O,O-dipropyl dithiophosphate); and the like. At present stannous 2-ethylhexanoate is preferred. Again, as with silicon and antimony, organic tin compounds are preferred over inorganic compounds.

Any of the listed sources of tin may be combined with any of the listed sources of silicon to form the combination of tin and silicon antifoulant or the combination of tin, antimony and silicon antifoulant. In like manner, any of the listed sources of anitmony may be combined with any of the listed sources of silicon to form the combination of antimony and silicon antifoulant or the combination of tin, antimony and silicon antifoulant.

Any suitable concentration of antimony in the combination of antimony and silicon antifoulant may be utilized. A concentration of antimony in the range of about 10 mole percent to about 90 mole percent is presently preferred because the effect of the combination of antimony and silicon antifoulant is reduced outside of this range. In like manner, any suitable concentration of tin may be utilized in the combination of tin and silicon antifoulant. A concentration of tin in the range of about 10 mole percent to about 90 mole percent is presently preferred because the effect of the combination of tin and silicon antifoulant is reduced outside of this range.

Any suitable concentration of antimony in the combination of tin, antimony and silicon antifoulant may be utilized. A concentration of antimony in the range of about 20 mole percent to about 60 mole percent is believed to be preferred. In like manner, a concentration of silicon in the range of about 20 mole percent to about 60 mole percent is believed to be preferred.

In general, the antifoulants of the present invention are effective to reduce the buildup of coke on any of the high temperature steels. Commonly used steels in cracking tubes are Incoloy 800, Inconel 600, HK40, 1¼ chromium-¾ molybdenum steel, and Type 304, Stainless Steel. The composition of these steels in weight percent is as follows:

cracking tubes for any suitable length of time. A time of at least about one minute is preferred to insure that all of the surface of the cracking tube has been treated. The contact time would typically be about ten minutes or longer in a commercial operation. However, it is not believed that the longer times are of any substantial benefit other than to fully assure an operator that the cracking tube has been treated.

It is typically necessary to spray or brush the antifoulant solution on the Metals to be treated other than the cracking tubes but flooding can be used if the equipment can be subjected to flooding.

Any suitable solvent may be utilized to prepare the solution of antifoulant. Suitable solvents include water, oxygen-containing organic liquids such as alcohols, ketones and esters and aliphatic and aromatic hydrocarbons and their derivatives. The presently preferred solvents are normal hexane and toluene although kerosene would be a typically used solvent in a commercial operation.

Any suitable concentration of the antifoulant in the solution may be utilized. It is desirable to use a concentration of at least 0.1 molar and concentrations may be 1 molar or higher with the strength of the concentrations being limited by metallurgical and economic considerations. The presently preferred concentration of antifoulant in the solution is in the range of about 0.2 molar to about 0.5 molar.

Solutions of antifoulants can also be applied to the surfaces of the cracking tube by spraying or brushing when the surfaces are accessible but application in this manner has been found to provide less protection against coke deposition than immersion. The cracking tubes can also be treated with finely divided powders of the antifoulants but, again, this method is not considered to be particularly effective.

In addition to pretreating of the Metals with the antifoulant or as an alternate method of contacting the Metals with the antifoulant, any suitable concentration of the antifoulant may be added to the feed stream flowing through the cracking tube. A concentration of antifoulant in the feed stream of at least ten parts per million by weight of the metal(s) contained in the antifoulant based on the weight of the hydrocarbon portion of the feed stream should be used. Presently preferred concentrations of antifoulant metals in the feed stream are in the range of about 20 parts per million to about 100 parts per million based on the weight of the hydro-

| STEEL | Ni | Cu | C | Fe | S | Cr | Mo | P | Mn | Si |
|---|---|---|---|---|---|---|---|---|---|---|
| Inconel 600 | 72 | .5 | .15 | 8.0 | | 15.5 | | | | |
| Incoloy 800 | 32.5 | .75 | .10 | 45.6 | | 21.0 | | 0.04 max | | |
| HK-40 | 19.0–22.0 | | 0.35–0.45 | balance ≅50 | 0.40 max | 23.0–27.0 | | | 1.5 max | 1.75 max |
| 1¼Cr—½Mo | | | | balance ≅98 | 0.40 max | 0.99–1.46 | 0.40–0.65 | 0.035 max | 0.36–0.69 | 0.13–0.32 |
| 304SS | 9.0 | | .08 | 72 | | 19 | | | | |

The antifoulants of the present invention may be contacted with the Metals either by pretreating the Metals with the antifoulant, adding the antifoulant to the hydrocarbon containing feedback or preferably both.

If the Metals are to be pretreated, a preferred pretreatment method is to contact the Metals with a solution of the antifoulant. The cracking tubes are preferably flooded with the antifoulant. The antifoulant is allowed to remain in contact with the surface of the carbon portion of the feed stream. Higher concentrations of the antifoulant may be added to the feed stream but the effectiveness of the antifoulant does not substantially increase and economic considerations generally preclude the use of higher concentrations.

The antifoulant may be added to the feed stream in any suitable manner. Preferably, the addition of the antifoulant is made under conditions whereby the antifoulant becomes highly dispersed. Preferably, the antifoulant is injected in solution through an orifice under pressure to atomize the solution. The solvents previously discussed may be utilized to form the solutions. The concentration of the antifoulant in the solution should be such as to provide the desired concentration of antifoulant in the feed stream.

Steam is generally utilized as a diluent for the hydrocarbon containing feedstock flowing to the cracking furnace. The stream/hydrocarbon molar ratio is considered to have very little effect on the use of the antifoulants of the present invention.

The cracking furnace may be operated at any suitable temperature and pressure. In the process of steam cracking of light hydrocarbons to ethylene, the temperature of the fluid flowing through the cracking tubes increases during its transit through the tubes and will attain a maximum temperature at the exit of the cracking furnace of about 850° C. The wall temperature of the cracking tubes will be higher and may be substantially higher as an insulating layer of coke accumulate within the tubes. Furnace temperatures of nearly 2000° C. may be employed. Typical pressures for a cracking operation will generally be in the range of about 10 to about 20 psig at the outlet of the cracking tube.

Before referring specifically to the examples which will be utilized to further illustrate the present invention, the laboratory apparatus will be described by referring to FIG. 1 in which a 9 millimeter quartz reactor 11 is illustrated. A part of the quartz reactor 11 is located inside the electric furnace 12. A metal coupon 13 is supported inside the reactor 11 on a two millimeter quartz rod 14 so as to provide only a minimal restriction to the flow of gases through the reactor 11. A hydrocarbon feed stream (ethylene) is provided to the reactor 11 through the combination of conduit means 16 and 17. Air is provided to the reactor 11 through the combination of conduit means 18 and 17.

Nitrogen flowing through conduit means 21 is passed through a heated saturator 22 and is provided through conduit means 24 to the reactor 11. Water is provided to the saturator 22 from the tank 26 through conduit means 27. Conduit means 28 is utilized for pressure equalization.

Steam is generated by saturating the nitrogen carrier gas flowing through the saturator 22. The steam/nitrogen ratio is varied by adjusting the temperature of the electrically heated saturator 22.

The reaction effluent is withdrawn from the reactor 11 through conduit means 31. Provision is made for diverting the reaction effluent to a gas chromatograph as desired for analysis.

In determining the rate of coke deposition on the metal coupon, the quantity of carbon monoxide produced during the cracking process was the considered to be proportional to the quantity of coke deposited on the metal coupon. The rationale for this method of evaluating the effectiveness of the antifoulants was the assumption that carbon monoxide was produced from deposited coke by the carbon-steam reaction. Metal coupons examined at the conclusion of cracking runs bore essentially no free carbon which supports the assumption that the coke had been gasified with steam.

The selectivity of the converted ethylene to carbon monoxide was calculated according to equation 1 in which nitrogen was used as an internal standard.

$$\% \text{ Selectivity (CO)} = \frac{(\text{mole \% CO/mole \% } N_2) \times 100}{\text{Conversion}} \quad (1)$$

The conversion was calculated according to equation 2.

$$\text{Conversion} = \frac{(\text{mole \% } C_2H_4/\text{mole \% } N_2)_{Feed} - (\text{mole \% } C_2H_4/\text{mole \% } N_2)_{sample}}{(\text{mole \% } C_2H_4/\text{mole \% } N_2)_{Feed}} \quad (2)$$

The CO level for the entire cycle was calculated as a weighted average of all the analyses taken during a cycle according to equation 3.

$$\text{Time Weighted Selectivity} = \frac{\Sigma \text{Selectivity} \times \text{Time}^{\frac{1}{2}}}{\Sigma \text{Time}^{\frac{1}{2}}} \quad (3)$$

The percent selectivity is directly related to the quantity of carbon monoxide in the effluent flowing from the reactor.

EXAMPLE 1

Incoloy 800 coupons, $1'' \times \frac{1}{4}'' \times 1/16''$, were employed in this example. Prior to the application of a coating, each Incoloy 800 coupon was thoroughly cleaned with acetone. Each antifoulant was then applied by immersing the coupon in a minimum of 4 mL of the antifoulant/solvent solution for 1 minute. A new coupon was used for each antifoulant. The coating was then followed by heat treatment in air at 700° C. for 1 minute to decompose the antifoulant to its oxide and to remove any residual solvent. A blank coupon, used for comparisons, was prepared by washing the coupon in acetone and heat treating in air at 700° C. for 1 minute without any coating. The preparation of the various coatings are given below.

0.5M Sb: 2.76 g of antimony 2-ethylhexanoate, $Sb(C_8H_{15}O_2)_3$, were mixed with enough toluene to make 10.0 mL of solution, referred to hereinafter as solution A.

0.5M Sn: 2.02 g of tin 2-ethylhexanoate, $Sn(C_8H_{15}O_2)_2$, were dissolved in enough toluene to make 10.0 mL of solution, referred to hereinafter as solution B.

0.5M Si: 1.04 g of tetraethylorthosilicate, $Si(OC_2H_5)_4$, were mixed with enough toluene to make 10.0 mL of solution, referred to hereinafter as solution C.

0.5M Sn-Si: 1.02 g of tin 2-ethylhexanoate, $Sn(C_8H_{15}O_2)_2$, and 0.52 g of tetraethylorthosilicate, $Si(OC_2H_5)_4$, were dissolved in enough toluene so as to make 10.0 mL of solution, referred to hereinafter as solution D.

0.5M Sb-Si: 1.36 g of antimony 2-ethylhexanoate, $Sb(C_8H_{15}O_2)_3$, and 0.52 g of tetraethylorthosilicate, $Si(OC_2H_5)_4$, were dissolved in enough toluene to make 10.0 mL of solution, referred to hereinafter as solution E.

0.5M Sn-Sb-Si: 0.68 g of tin 2-ethylhexanoate, $Sn(C_8H_{15}O_2)_2$, 0.93 g of antimony 2-ethylhexanoate, $Sb(C_8H_{15}O_2)_3$, and 0.34 g of tetraethylorthosilicate, $Si(OC_2H_5)_4$, were dissolved in enough toluene to make 10.0 mL of solution, referred to hereinafter as solution F.

The temperature of the quartz reactor was maintained so that the hottest zone was 900±5° C. A coupon was placed in the reactor while the reactor was at reaction temperature.

A typical run consisted of three 20 hour coking cycles (ethylene, nitrogen and steam), each of which was followed by a 5 minute nitrogen purge and a 50 minute decoking cycle (nitrogen, steam and air). During a coking cycle, a gas mixture consisting of 73 mL per minute ethylene, 145 mL per minute nitrogen and 73 mL per minute steam passed downflow through the reactor. Periodically, snap samples of the reactor effluent were analyzed in a gas chromatograph. The steam/hydrocarbon molar ratio was 1:1.

Table I summarizes results of cyclic runs (with from 1 to 3 cycles) made with Incoloy 800 coupons that had been immersed in the previously described test solutions A-F.

TABLE I

| | | Time Weighted Selectivity to CO | | |
|---|---|---|---|---|
| Run | Solution | Cycle 1 | Cycle 2 | Cycle 3 |
| 1 | None (Control) | 19.9 | 21.5 | 24.2 |
| 2 | A | 15.6 | 18.3 | — |
| 3 | B | 5.6 | 8.8 | 21.6 |
| 4 | C | 11.9 | 25.1 | 27.3 |
| 5 | D | 2.8 | 4.3 | 10.8 |
| 6 | E | 1.2 | — | 6.2 |
| 7 | E$^a$ | 3.0 | 4.8 | 8.6 |
| 8 | E | 2.1 | 5.8 | 8.2 |
| 9 | F | 4.4 | 8.8 | 15.3 |

$^a$Runs 7 and 8 were tested using Solution E due to the loss of the data for the second cycle of run 6.

The results of runs 2, 3 and 4 in which tin, antimony and silicon were used separately, show that only tin was effective in substantially reducing the rate of carbon deposition on Incoloy 800 under conditions simulating those in an ethane cracking process. However, binary combinations of these elements used in runs 5 through 8 show some very surprising effects. Run 5, in which tin and silicon were combined, shows that this combination is more effective than would be expected from the results of runs in which tin or silicon were used alone. Runs 6–8, in which antimony and silicon were combined, shows that this combination is substantially more effective than either antimony or silicon alone. Run 9, in which the trinary combination of tin, antimony and silicon was used, shows that the trinary combination was also more effective than either tin, antimony or silicon used alone.

EXAMPLE 2

Using the process conditions of Example 1, a plurality of cycle runs were made using antifoulants which contained different ratios of tin and silicon and different ratios of antimony and silicon. Each run employed a new Incoloy 800 coupon which had been cleaned and treated as described in Example 1. The antifoulant solutions were prepared as described in Example 1 with the exception that the ratio of the elements was varied. The results of these tests are illustrated in FIG. 2 and FIG. 3.

Figure 2:
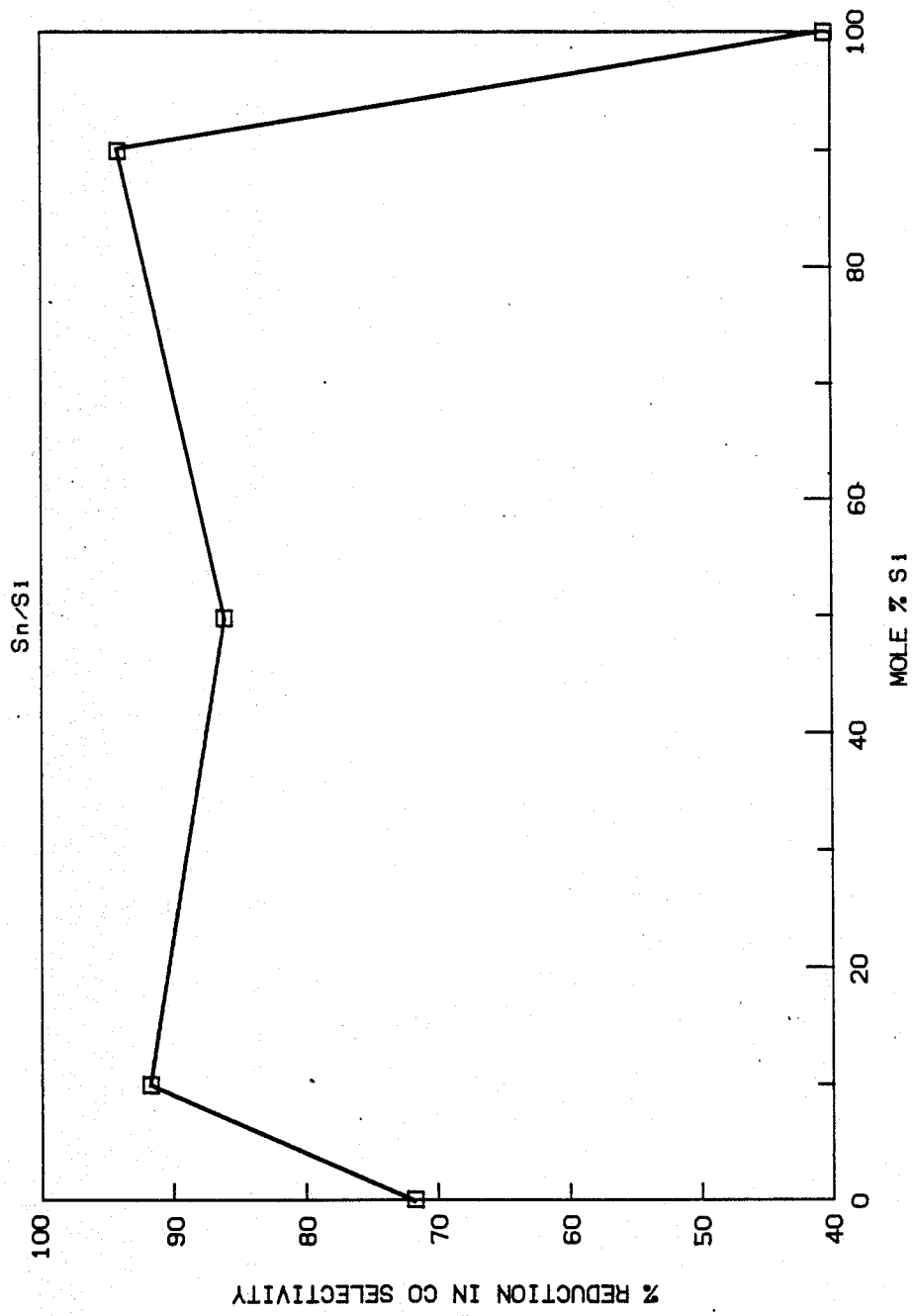
FIG. 2 is a graphical illustration of the effect of a combination of tin and silicon.
Figure 3:
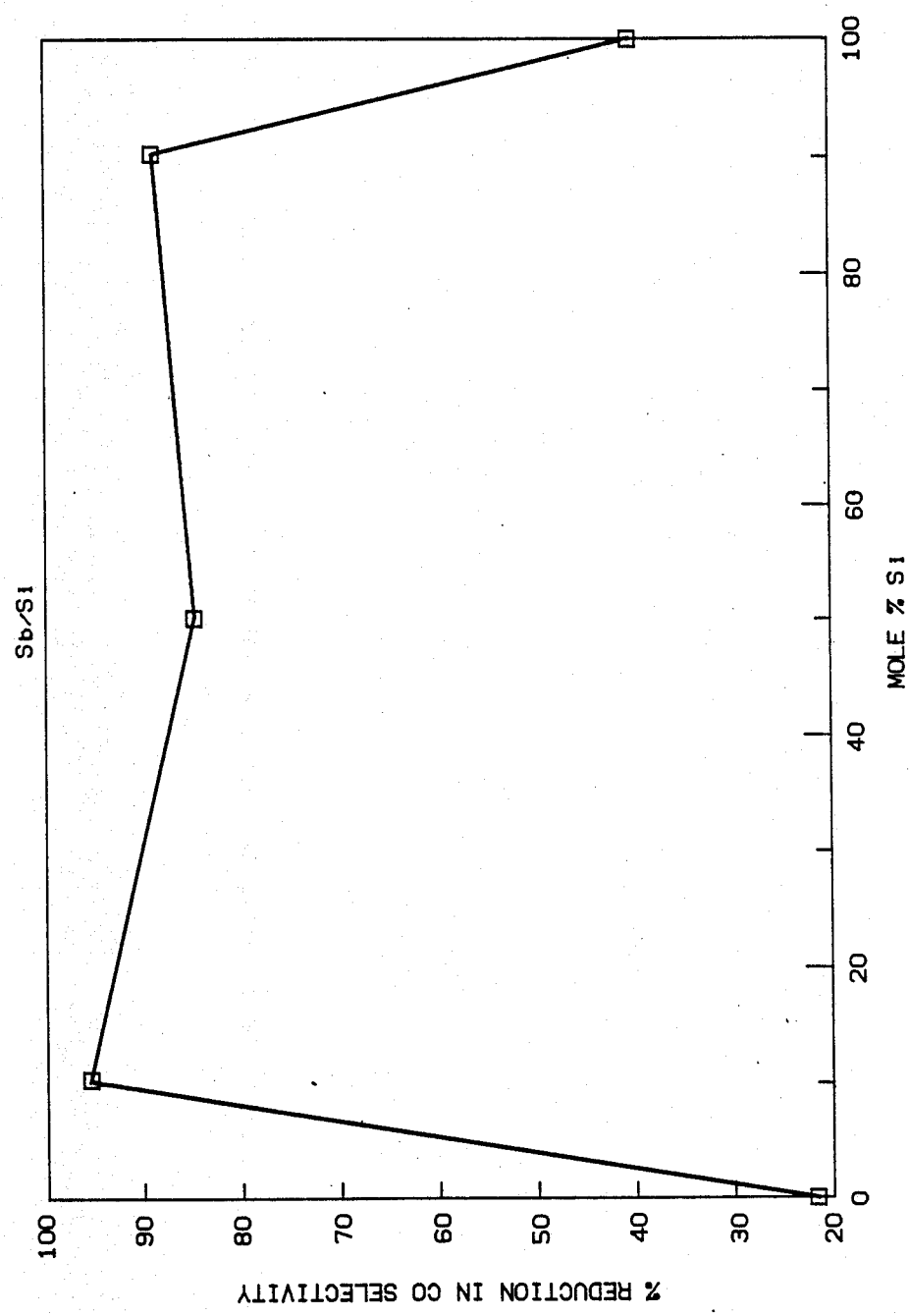
FIG. 3 is a graphical illustration of the effect of a combination of anitmony and silicon.

Referring to FIG. 2, it can be seen that the combination of tin and silicon was particularly effective when the concentration of silicon was in the range from about 10 mole percent to about 90 mole percent. Outside of this range, the effectiveness of the combination of tin and silicon was reduced.

Referring now to FIG. 3, it can again be seen that the combination of antimony and silicon was effective when the concentration of silicon was in the range of about 10 mole percent to about 90 mole percent. Again, the effectiveness of the combination of antimony and silicon is reduced outside of this range.

Reasonable variations and modifications are possible by those skilled in the art within the scope of the described invention and the appended claims.

That which is claimed is:

1. A method for reducing the formation of coke on the metals which are contacted with a gaseous stream containing hydrocarbons in a thermal cracking process comprising the step of contacting said metals with an antifoulant selected from the group consisting of a composition comprising silicon and tin, a composition comprising silicon and antimony and a composition comprising silicon, tin and antimony, wherein said silicon, tin and antimony are present in said composition in a form selected from the group consisting of elemental metals, organic compounds and inorganic compounds.

2. A method in accordance with claim 1 wherein said step of contacting said metals with said antifoulant comprises contacting said metals with a solution of said antifoulant when said gaseous stream is not in contact with said metals.

3. A method in accordance with claim 2 wherein said metals are contacted with said solution for at least about 1 minute and wherein the concentration of said antifoulant in said solution is at least about 0.1 molar.

4. A method in accordance with claim 3 wherein ther concentration of said antifoulant in said solution is in the range of about 0.2 molar to about 0.5 molar.

5. A method in accordance with claim 2 wherein the solvent used to form the solution of said antifoulant is selected from the group consisting of water, oxygen-containing organic liquids and aliphatic and aromatic hydrocarbons.

6. A method in accordance with claim 2 wherein said step of contacting said metals with said antifoulant additionally comprises the step of adding a suitable amount of said antifoulant to said gaseous stream before said metals are contacted with said gaseous stream.

7. A method in accordance with claim 6 wherein the concentration by weight of said antifoulant in said gaseous stream is at least ten parts per million by weight of antifoulant metals based on the weight of the hydrocarbons in said gaseous stream.

8. A method in accordance with claim 6 wherein the concentration by weight of said antifoulant in said gaseous stream is at least twenty parts per million by weight of antifoulant metals based on the weight of the hydrocarbons in said gaseous stream.

9. A method in accordance with claim 6 wherein said antifoulant is added to said gaseous stream by injecting a solution of said antifoulant through an orifice under pressure so as to atomize said solution.

10. A method in accordance with claim 1 wherein said step of contacting said metals with said antifoulant comprises the step of adding a suitable amount of said antifoulant to said gaseous stream before said metals are contacted with said gaseous stream.

11. A method in accordance with claim 10 wherein the concentration by weight of said antifoulant in said gaseous stream is at least ten parts per million by weight of antifoulant metal based on the weight of the hydrocarbons in said gaseous stream.

12. A method in accordance with claim 10 wherein the concentration by weight of said antifoulant in said gaseous stream is at least twenty parts per million by weight in antifoulant metal based on the weight of the hydrocarbons in said gaseous stream.

13. A method in accordance with claim 10 wherein said antifoulant is added to said gaseous stream by injecting a solution of said antifoulant through an orifice under pressure so as to atomize said solution.

14. A method in accordance with claim 1 wherein the concentration of silicon in said composition comprising silicon and tin and said composition comprising silicon and antimony is in the range of about 10 mole percent to about 90 mole percent and wherein the concentration of antimony and silicon in said composition comprising tin, antimony and silicon is in the range of about 20 mole percent to about 60 mole percent for both said antimony and said silicon.

15. A composition that is suitable as an antifoulant selected from the group consisting of a composition comprising silicon and tin, a composition comprising silicon and antimony and composition comprising silicon, tin and antimony, wherein said silicon, tin and antimony are present in said compositions in a form selected from the group consisting of elemental metals, organic compounds and inorganic compounds and in a form which is further characterized by being convertible to an oxide when contacted with air at a temperature of about 700° C.

16. A composition in accordance with claim 15 wherein said composition comprises silicon and tin.

17. A composition in accordance with claim 16 wherein the concentration of tin in said composition is in the range of about 10 mole percent to about 90 mole percent.

18. A composition in accordance with claim 16 wherein said composition comprises tetraethylorthosilicate and stannous 2-ethylhexanoate.

19. A composition in accordance with claim 15 wherein said composition comprises silicon and antimony.

20. A composition in accordance with claim 19 wherein the concentration of antimony in said composition is in the range of about 10 mole percent to about 90 mole percent.

21. A composition in accordance with claim 19 wherein said composition comprises tetraethylorthosilicate and antimony 2-ethylhexanoate.

22. A composition in accordance with claim 15 wherein said composition comprises silicon, tin and antimony.

23. A composition in accordance with claim 22 wherein the concentration of antimony and silicon in said composition is in the range of about 20 mole percent to about 60 mole percent for both said antimony and said silicon.

24. A composition in accordance with claim 22 wherein said composition comprises tetraethylorthosilicate, stannous 2-ethylhexanoate and antimony 2-ethylhexanoate.

25. A composition in accordance with claim 15 wherein said composition is in a solution and wherein the concentration of said composition in said solution is at least about 0.1 molar.

26. A composition in accordance with claim 25 wherein the concentration of said composition in said solution is in the range of about 0.3 molar to about 0.6 molar.

27. A composition in accordance with claim 25 wherein the solvent used to form the solution of said composition is selected from the group consisting of water, oxygen-containing organic liquids and aliphatic and aromatic hydrocarbons.

28. A composition in accordance with claim 16 wherein said composition consists essentially of silicon and tin.

29. A composition in accordance with claim 19 wherein said composition consists essentially of silicon and antimony.

30. A composition in accordance with claim 22 wherein said compositions consists essentially of silicon, tin and antimony.

* * * * *